United States Patent [19]
Pfund

[11] Patent Number: 5,686,652
[45] Date of Patent: Nov. 11, 1997

[54] PORTABLE TEST HAMMER APPARATUS

[76] Inventor: Bruce Pfund, 7 Windover Turn, Westerly, R.I. 02891

[21] Appl. No.: 707,851

[22] Filed: Sep. 9, 1996

[51] Int. Cl.$^6$ .................................................. G01M 7/00
[52] U.S. Cl. ........................ 73/12.04; 73/12.07; 73/79; 73/82
[58] Field of Search ................... 73/12.01, 12.03, 73/12.04, 12.07, 78, 79, 81, 82, 12.12, 85

[56] References Cited

U.S. PATENT DOCUMENTS

| | | |
|---|---|---|
| 3,352,143 | 11/1967 | Bollar . |
| 3,354,693 | 11/1967 | Asari . |
| 3,473,371 | 10/1969 | Loeb ........................... 73/12.01 |
| 3,597,969 | 8/1971 | Curchack . |
| 3,793,874 | 2/1974 | Shockey et al. . |
| 3,823,600 | 7/1974 | Wolff . |
| 3,998,090 | 12/1976 | Wislocki . |
| 4,201,078 | 5/1980 | Morinaga . |
| 4,349,200 | 9/1982 | Wakefield . |
| 4,433,570 | 2/1984 | Brown et al. . |
| 4,470,293 | 9/1984 | Redmon . |
| 4,542,639 | 9/1985 | Cawley et al. . |
| 4,674,318 | 6/1987 | Bourdon . |
| 5,025,655 | 6/1991 | Umemura et al. . |
| 5,048,320 | 9/1991 | Mitsuhashi et al. ............ 73/12.09 |
| 5,184,499 | 2/1993 | Oppliger et al. . |
| 5,247,835 | 9/1993 | Howell ........................... 73/12.01 |
| 5,277,055 | 1/1994 | Pittard et al. . |
| 5,311,764 | 5/1994 | Smith et al. .................... 73/12.04 |
| 5,311,856 | 5/1994 | White et al. . |
| 5,400,640 | 3/1995 | Stuckey . |
| 5,404,755 | 4/1995 | Olson et al. .................... 73/12.12 |
| 5,410,905 | 5/1995 | Karani et al. . |
| 5,438,872 | 8/1995 | Kobayashi et al. .............. 73/12.01 |

FOREIGN PATENT DOCUMENTS

| | | | |
|---|---|---|---|
| 2695206 | 4/1994 | France ............................ 73/12.11 |
| 5984153 | 5/1984 | Japan ............................. 73/12.12 |

Primary Examiner—Ronald Biegel
Attorney, Agent, or Firm—Salter & Michaelson

[57] ABSTRACT

A portable test hammer apparatus that produces repeatable and adjustable impacts to make traditional "tap testing" more reliable and quantified. The apparatus includes an impactor head device having a housing sized to be held in a human hand and engageable with the structural member, a plurality of adaptor bases, each readily mounted on the housing, an impactor head disposed within the housing for reciprocating movement therein, and a fluid piston assembly for moving the impactor head from a retracted position within the housing to a projected position in which the impactor head impacts the structural member. Impactor devices can be rapidly slid across test surfaces on non-marring feet, vacuum adhered to the test surface, or both. The apparatus further includes a rugged acoustic transducer for generating and transmitting an electrical signal based on the acoustic signature of the strike of the impactor head against the structural member. An acoustic spectral analyzer characterizes the acoustic signatures of the impacts, with extensive filtering and modeling options that configure the processing to best emphasize differences between intact and damaged test areas. A monitor and tape recording machine are further provided for displaying the test results, and playing the results back, respectively.

20 Claims, 10 Drawing Sheets

PORTABLE TEST HAMMER APPARATUS

BACKGROUND OF THE INVENTION

This invention relates generally to apparatus capable of testing the structural integrity of materials, and more particularly to a portable apparatus which is especially suited for field use or use on non-flat, contoured surfaces, and produces more repeatable, quantitative and easily interpreted, non-subjective results than prior art apparatus.

Generally, the present invention is directed to the use of tap testing or "hammer sounding" as a method for analyzing structures and searching for damage, voids or de-laminations in solid or cored structures. Examples of fields where manual tap testing is currently in service are: locating internal framing in metallic, wood and composite construction; flight line checks of composite control surfaces on military and commercial aircraft; checking for voids in composite helicopter blades; checking for loose fasteners and skin de-lamination in cored or solid composite aircraft and marine structures; and hollowness in other materials. Careful "tuning" of both impact energy and the material used for the impactor head are required to generate acoustic signatures that most readily characterize the differences between good and damaged areas. Artisan hammer sounders may carry multiple hammers, each being optimized for testing a certain structure or material. A "good ear" and years of experience is required, and the wide range of tap energies, tap head materials and test item configurations has left manual tap testing a non-quantified skill, most suitable for use in testing many similar parts, so the operator learns its acoustic signature.

One advantage to manual tap testing as opposed to other types of modern testing readily available is rapid assessment of large areas. Cumbersome laboratory test equipment is unsuitable for use in conditions where large, complex shaped structures, such as military boats, ships and components, require testing. However, as mentioned above, manual tap testing oftentimes provides inconsistent and hence difficult to interpret results, especially for an operator who is not skilled in the art of tap testing.

Reference can be made to U.S. Pat. No. 4,542,639 to Cawley et al. as being representative of existing apparatus for testing the structural integrity of materials. Cawley et al. discloses an apparatus having a housing which is attached to a trolley. The housing supports a permanent magnet having a recess for slidably receiving a former assembly therein. The former assembly includes an impactor head which is associated with a force transducer and moved axially in an up-and-down direction for testing the structure. The assembly is electrically operated so that upon applying a current pulse to the assembly the head is moved towards the structure.

As illustrated in Cawley et al., leads connect the force transducer of the assembly to an amplifier for amplifying the signal created by the impact. This signal is manipulated by a fourier transform unit and displayed by monitor. It should be noted that the signal displayed from a damaged area can be compared to an undamaged reference structure. However, Cawley et al. fails to disclose an apparatus capable of recording and playing back prior test results.

A significant disadvantage associated with Cawley et al.'s apparatus is that it is relatively large and heavy and cannot be used in field applications. In this regard, the apparatus is limited to testing only horizontal test surfaces where it is registered against the test surface by its own weight. There is a need for a lightweight apparatus which is capable of being use during field applications where not only flat, horizontal surfaces are tested, but vertical and overhead surfaces, curved surfaces, corners and other contours can be tested as well.

Moreover, the Cawley et al. apparatus uses a force transducer coupled to the impact head for generating an output signal and transmitting the signal to the amplifier. Such a force transducer is subject to data scatter when testing rough surfaces. Additionally, the electrical impulses generated by Cawley et al.'s apparatus generate magnetic and electrical interference. Thus, the apparatus must be designed to electrically shield the force transducer and the cables extending therefrom to reduce interference and data errors. Also, the force transducer and its mechanical connection to the impactor head is subject to degradation after many cycles of use. Slight variations in the registration of the Cawley et al. impact generator and the variable coupling between the test surface and the impactor head create large force variations.

SUMMARY OF THE INVENTION

In general, the present invention is directed to a portable "tap testing" or test hammer apparatus for testing the structural integrity of a structural member. The apparatus comprises an impactor head device having a housing sized to be held in a human hand and engageable with the structural member, an impactor head disposed within the housing for reciprocating movement therein, and moving means for moving the impactor head from a retracted position within the housing to a projected position in which the impactor head impacts the structural member. Control logic valving and elastomeric bumpers are employed in the impactor head device to reduce its audible contribution to the impact's acoustic spectrum emissions. The apparatus further includes signal means for generating and transmitting an acoustic signal based on the impact of the impactor head against the structural member. In the present invention, the signal means embodies an acoustic transducer located proximate to the point of impact of the impactor head against the structural member. Unlike Cawley, the acoustic transducer is not directly coupled or attached to the impactor head device.

More specifically, the housing has a "doubleacting" mechanism comprising an upper head wall, a lower head wall spaced from the upper head wall, and a cylindrical wall attached at its upper end to the upper head wall and attached at its lower end to the lower head wall. The moving means comprises a piston attached to the impactor head wherein the piston is disposed within the chamber defined by the upper and lower head walls and the cylindrical wall for reciprocating movement therein. The moving means of the invention further comprises fluid delivery means in fluid communication with the chamber, the fluid delivery means embodying a first line connected to a first port formed in the cylindrical wall of the housing so as to deliver fluid into the chamber above the piston and a second line connected to a second port formed in the cylindrical wall so as to deliver fluid into the chamber below the piston.

Single or multiple durometer elastomeric bumpers and/or shock absorbers are placed within the chamber against the upper and lower head walls to cushion the piston mechanically at each end of its stroke to reduce the spurious noise generated by the impactor head device.

The housing further comprises a mounting plate attached to the lower head wall, the mounting plate having means for releasably securing thereto an attachment fixture for sliding on or adhering to the test member. There are many attachment fixtures for accommodating varying test surfaces. The attachment fixture has a body contoured to correspond with the surface of the structural member. The attachment fixture further has a plurality of positioning elements with low friction, non-marring pads secured to body for sliding on the surface of the structural member so that large areas can be rapidly inspected, and also for adjusting the height of the body relative to structural member.

In another aspect of the invention, the housing further has means for drawing the housing of the impactor head device against the surface of the structural member. The drawing means comprises an elastomeric seal secured to the lower head wall of the housing, and a vacuum source in fluid communication with the housing. Vacuum attachment increases the uniformity of test device registration to the test surface, further reducing variation in impact acoustic spectrum.

The apparatus further comprises control means for controlling the fluid delivering means. The control means includes, in one embodiment of the invention, a control suitcase having a valve and logic/adjustment controls for controlling the delivery of fluid into the first and second ports. For another embodiment of the invention, the control means is provided on a belt mounted unit which is worn by the operator of the apparatus. Further provided is a display means, in electrical communication with the signal means, for visually displaying the acoustic signal. The displaying means comprises a microprocessor, and acoustic spectral analyzer and a screen monitor.

Accordingly, among the several objects of the present invention are the provision of an apparatus for testing surfaces which is portable, light-weight and suitable for use during field applications or on components having widely varying surface contours; the provision of such an apparatus which is safe to use since it can be fluid operated (i.e., in this example, not electrically powered) and fabricated from non-sparking materials; the provision of such an apparatus which produces repeatable results that can be quantitatively compared to results obtained for structurally acceptable test areas; the provision of such an apparatus having multiple surface attachment fixtures for enabling the apparatus to fully engage various surfaces (e.g., flat surfaces, curved surfaces, and corners); the provision of such an apparatus which is relatively lightweight and easy to operate; the provision of such an apparatus which can test the structural integrity of large areas of material quickly; the provision of such an apparatus which can be operated to tightly seal with the surface that is being tested; and the provision of such an apparatus which is capable of processing and displaying test results on a computer screen, and replaying the test results.

Other objects, features and advantages of the invention shall become apparent as the description thereof proceeds when considered in connection with the accompanying illustrative drawings.

BRIEF DESCRIPTION OF THE DRAWINGS

In the drawings which illustrate the best mode presently contemplated for carrying out the present invention.

Corresponding reference numerals designate corresponding parts throughout the several views of the drawings.

DETAILED DESCRIPTION OF THE PREFERRED EMBODIMENTS

Figure 1:
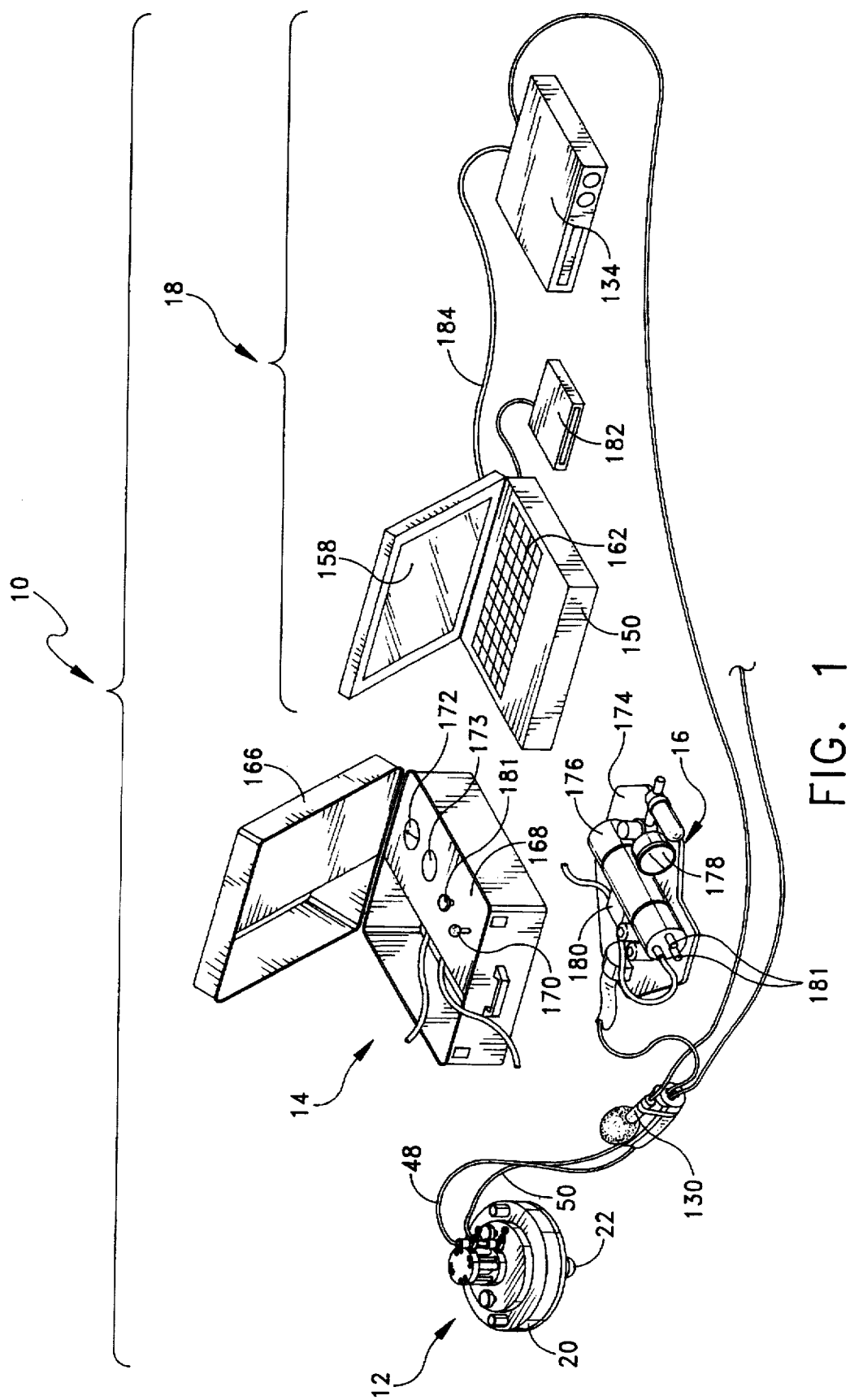
FIG. 1 is a perspective view of a portable test hammer apparatus of the present invention.

Referring now to the drawings, and more particularly to FIG. 1, there is generally indicated at 10 a portable test hammer apparatus of the present invention for testing the structural integrity of a structural member. As shown, the test hammer apparatus 10 comprises an impactor head device, generally indicated at 12, a first control, generally indicated at 14, which is in fluid communication with the impactor head device 12, a second control, generally indicated at 16, which can alternatively be used to control device 12 in place of the first control 14, and a microprocessor assembly, generally indicated at 18. The impactor head device 12 is sized so that it can be easily and conveniently held by a human hand, thereby enabling the device 12 to be used during field applications, such as testing structural members on a sea vessel, airplane or ship. Moreover, since the apparatus 10 utilizes an acoustic transducer de-coupled from the impactor head device 12, which will be described in greater detail as the detailed description proceeds, rather than a force transducer mechanically coupled to the head of the device, more repeatable and readily interpreted results produced by the apparatus 10 are achieved. The device 12 is more forgiving of many of the variables inherently present in field testing.

Figure 2:
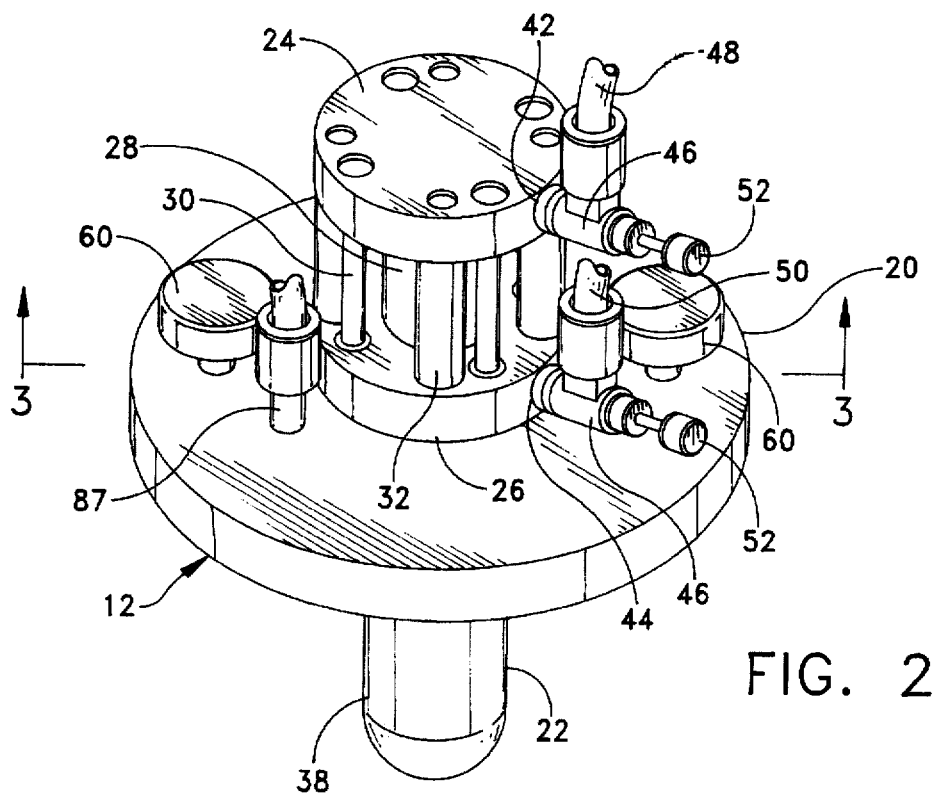
FIG. 2 is an enlarged perspective view of an impactor head device of the apparatus.
Figure 3:
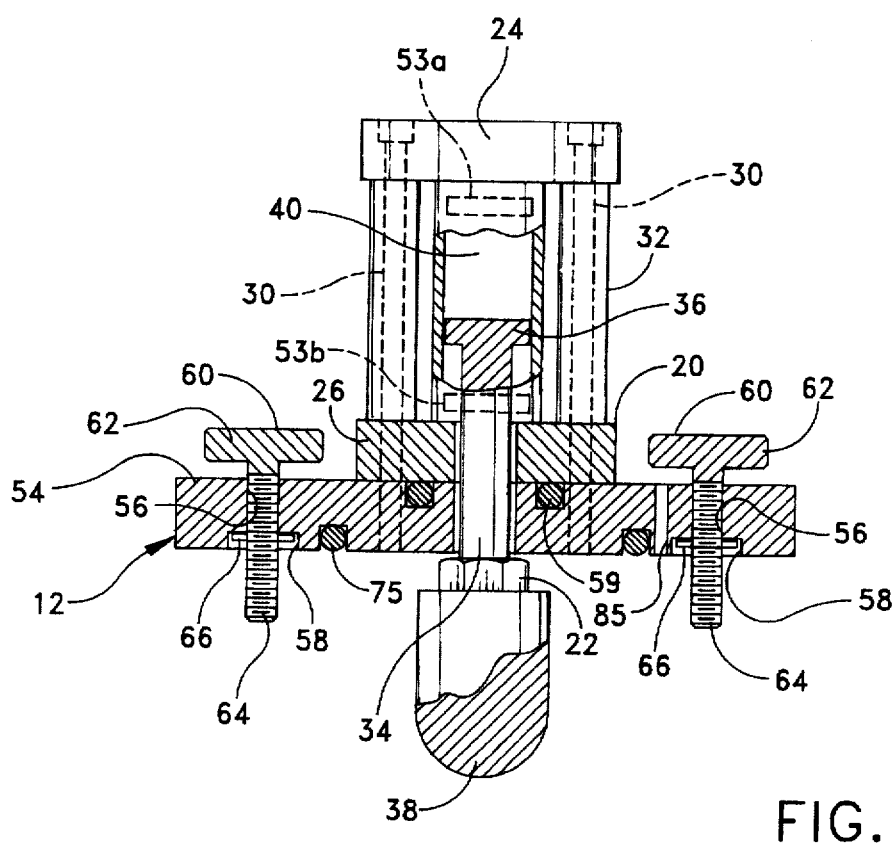
FIG. 3 is a cross-sectional view taken along line 3—3 of FIG. 2.

Turning now to FIGS. 2 and 3, the impactor head device 12 includes a housing 20 which is sized to be held or gripped within a human hand, and an impactor head 22 disposed within the housing 20 for reciprocating movement within the housing 20. More particularly, the housing 20 has an upper head wall 24, a lower head wall 26 that is spaced from the upper head wall 24, and a cylindrical wall 28 that is attached at its upper end to the upper head wall 24 and attached at its lower end to the lower head wall 26. Four bolts, each indicated at 30, interconnect the upper and lower head walls 24, 26. As shown, the support members 30 are spaced circumferentially around the cylindrical wall 28. Four additional support spacers, each indicated at 32, are further provided for additional strength and rigidity to the housing 20.

As best illustrated in FIG. 3, the impactor head 22 includes a shaft 34 having a piston 36 formed at one end thereof and a threaded end portion (not shown) at its other, opposite end. The impactor head 22 also includes a blunt head member 38 having a threaded bore (not shown) formed therein for threadably receiving the threaded end portion of the shaft 34. The head member 38 is releasably attached to the shaft 34 so that other types of head members made from different materials and having different sizes and weights can be attached to the shaft 34. As shown, the piston 36 is integrally formed with the cylindrical body of the shaft 34.

The upper head wall 24, lower head wall 26 and cylindrical wall 28 combine to define a chamber 40, which slidably receives the piston 36 of the shaft 34 therein for powering the movement of the impactor head 22 between an upwardly disposed, retracted position in which the head member 38 is substantially disposed within the housing 20 and a downwardly disposed, extended position in which the head member 38 strikes the surface of the structural member requiring testing.

First and second ports 42, 44 are formed in the upper and lower head walls 24, 26, respectively, As shown in FIG. 2, the first port 42 is attached to a cylinder flow control valve 46 in fluid communication with a first line 48 provided for delivering fluid (or liquid) to the chamber 40 above the piston 36. The valve 46 provides unrestricted flow through a check valve in one direction and variable (adjustable) flow through a needle valve in the other direction. Similarly, the second port 44 is attached to another valve, also indicated at 46, which is in fluid communication with a second line 50 adapted to deliver fluid to the chamber 40 below the piston 36. Each valve 46 has a knob 52 for controlling the rate of fluid delivery into the chamber 40 and thus the speed of the piston 36 reciprocally moving within the chamber 40.

The arrangement is such that upon either the first control 14 or the second control 16 delivering fluid to the first line 48, fluid is delivered to the chamber 40 above the piston 36 for moving the impactor head 22 downwardly. This motion of the piston 36 causes the impactor head member 38 to impact the structural member being tested. After the impact, fluid is then delivered by the first or second control 14, 16 to the second line 50 thereby delivering fluid into the chamber 40 below the piston 36 for moving the impactor head 22 upwardly to its retracted position. The speed of the impactor head 22 stroke is controlled by the knobs 52 provided on the valves 46 and by supply pressure. As mentioned briefly above, the apparatus 10 preferably is pneumatically driven; however, other fluids can be used as well, such as hydraulic fluid or water. Moreover, a series of solenoids, induction motors, or other similar apparatus known in the art, can be provided for driving the movement of the impactor head between its retracted and extended positions and still fall within the scope of the present invention.

As the unit is designed to produce repeatable, impact generated audible signatures, measures have been taken to reduce spurious noise created by operation of the impactor head device 12. Accordingly, multiple durometer impact absorbing bumpers 53a, 53b are disposed within the chamber 40 adjacent the upper and lower head walls 24, 26, respectively. These bumpers 53a, 53b are illustrated in broken lines in FIG. 3. As shown, the piston 36, upon moving in an upstroke direction, engages the bumper 53a so as to cushion and reduce the force and noise of impact of the piston 36 against the upper head wall 24. Similarly, bumper 53b cushions and reduces the force of impact of the piston 36 against the lower head wall 26.

The housing 20 of the impactor head device 12 further includes a mounting plate 54 that is attached to the lower head wall 26 of the housing 20. As shown in FIG. 3, the support members 30 extend through the lower head wall 26 and are threadably secured to the mounting plate 54 for attaching the mounting plate 54 to the housing 20. A gasket or seal 59 seals the lower head wall 26 and the mounting plate 54. The mounting plate 54 has multiple clearance bores 56 formed therein, each with a counterbore 58 formed on the bottom surface of the mounting plate 54. Each clearance bore 56 receives a thumb turn fastener 60 having an enlarged knurled head 62 and a threaded bolt 64 extending downwardly from the head 62 through the clearance bore 56. A retainer clip 66 is provided for retaining the thumb turn fastener 60 to the mounting plate 54.

Figure 4:
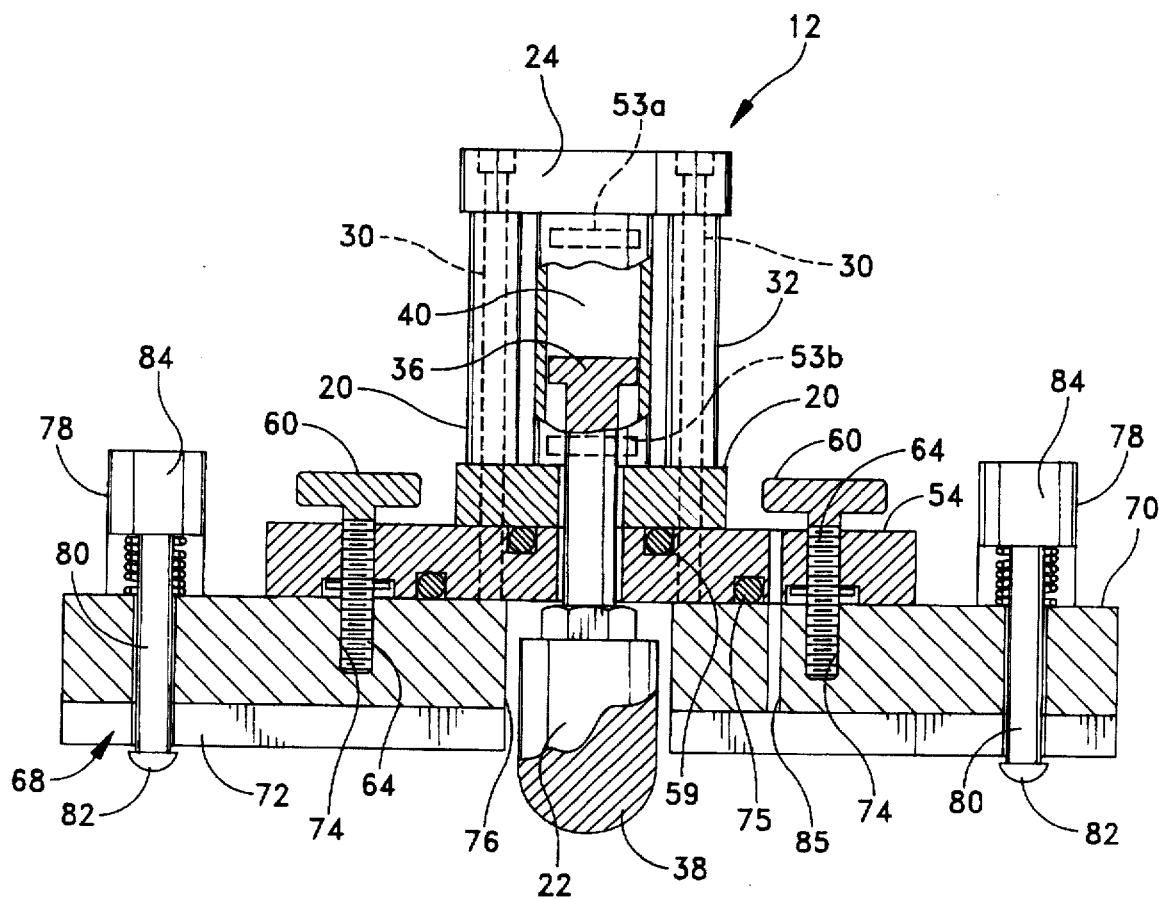
FIG. 4 is a cross-sectional view, similar to FIG. 3, illustrating the device with a flat surface attachment fixture mounted thereon, with extendable/retractable low friction slider feet and an elastomeric gasket for vacuum sealing to the test article surface.

Referring now to FIG. 4, the impactor head device 12 illustrated in FIGS. 2 and 3 is shown attached to a flat fixture, generally indicated at 68, which is releasably secured to the mounting plate 54 for engaging the structural member. The attachment fixture 68 has a disk-shaped body 70 with an elastomeric gasket or seal 72, fabricated from material suitably compliant to seal to the test surface, fixedly secured thereto to establish a vacuum seal between the body 70 and the surface of the structure being tested. The body 70 has multiple threaded bores 74 formed therein for threadably receiving the threaded bolts 64 of the thumb turn fasteners 60. Another gasket or seal 75 seals the body 70 of the fixture 68 to the mounting plate 54. The body 70 further includes a larger, centrally located opening 76 formed therein, through which the impactor head 22 extends.

The attachment fixture 68 further includes a plurality of positioning elements 78 that are secured to the body 70 for registering on the surface of the structural member to adjust the height of the body 70 and gasket 72 relative to the structural member and to allow it to slide when elements 78 are extended. As shown, each positioning member 78 includes a cylindrical shaft portion 80 having a non-marring end or foot 82 provided on its lower end, and a mechanism 84 disposed above the shaft portion 80 and fixedly mounted on the body 70 for adjusting the height of the shaft portion 80. The arrangement is such that by adjusting each mechanism 84, the length of the shaft portion 80 projecting beyond the gasket 72 of the body 70 is adjusted. The positioning elements 78 each comprise a self retracting actuator that controls the position of the low friction foot 82. When multiple feet 82 are extended, the device 12 is readily slid across the test surface as the impactor head 22 reciprocates to rapidly inspect larger areas. When elements 82 are retracted, the elastomeric vacuum seal gasket 72 contacts the test surface and the unit 12 can then be vacuum adhered to the surface in the manner described below.

In this regard, the housing 20 of the impactor head device 12 is provided with a means for drawing the housing 20 and the fixture 68 against the surface of the structural member. More particularly, there is a passageway 85 formed in the mounting plate 54 and the body 70 of the fixture 68 in fluid communication with a line 87 suitably connected to a vacuum source (not shown). The arrangement is such that upon connecting the passageway 85 with the line connected to the vacuum source, and engaging the vacuum source, an airtight seal is formed by the elastomeric seal 72 between the fixture 68 and the structural member being tested. This provides a more secure positioning of the impactor head device 12 against the structural member thereby increasing the uniformity of the acoustic returns generated by the impactor head member striking the test surface.

Figure 5A:
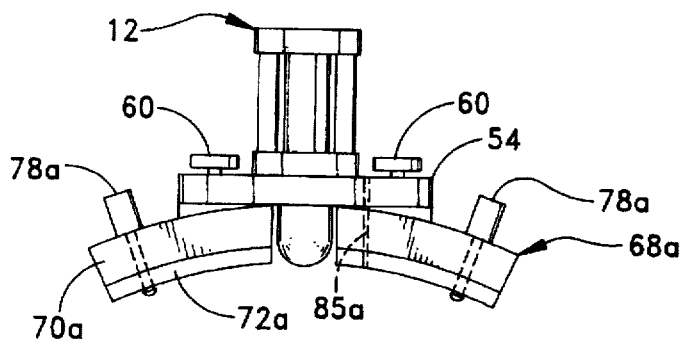
FIGS. 5A–5E are elevational views illustrating a plurality of surface attachment fixtures that are mounted on the impactor head device.
Figure 5B:
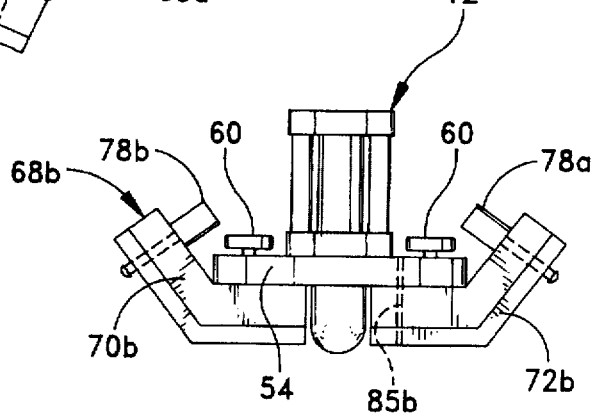
Figure 5C:
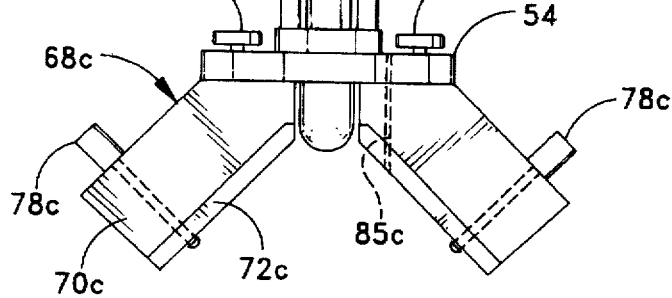
Figure 5D:
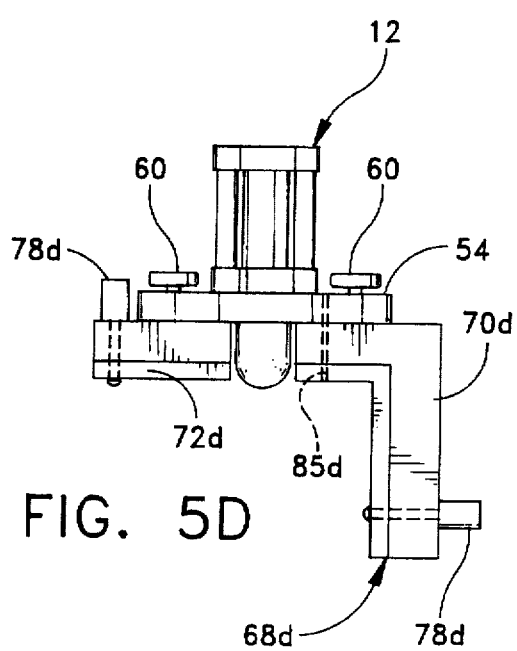
Figure 5E:
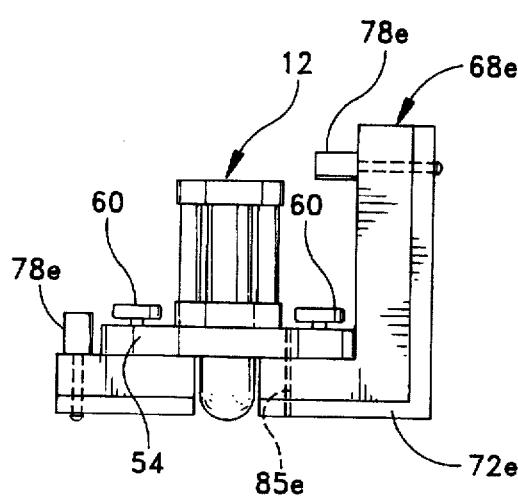

In FIGS. 5A–5E, there are illustrated several embodiments of attachment fixtures for accommodating varying surface shapes. The impactor head device 12 rapidly mounts to any of these attachment fixtures 68a–68e without the aid of tools by thumb turn fasteners 60. In FIG. 5A, there is illustrated an attachment fixture 68a having a body 70a with a curved or radiused body. The body 70a can be configured with manually adjustable height low friction, non-marring positioning elements 78a, which are extendable and retractable depending upon whether the device 12 is attached to the vacuum source. In this regard, each fixture 68a–68e includes a passageway 85a–85e, respectively, for enabling the device to be connected to the vacuum source. This attachment fixture 68a is especially suited for engaging structural members having curved surfaces. In FIG. 5B, an attachment fixture 68b having a body 70b with upwardly flaring ends is provided. This fixture 68b is for locating the impactor head device in an inside corner of the structural member requiring testing. FIGS. 5C–5E illustrate attachment fixtures 68c, 68d, and 68e, respectively, each being constructed for a particular purpose. It should be noted that attachment fixtures of various shapes and sizes corresponding to varying size and configurations of test surfaces can be provided and still fall within the scope of the present invention.

Figure 6:
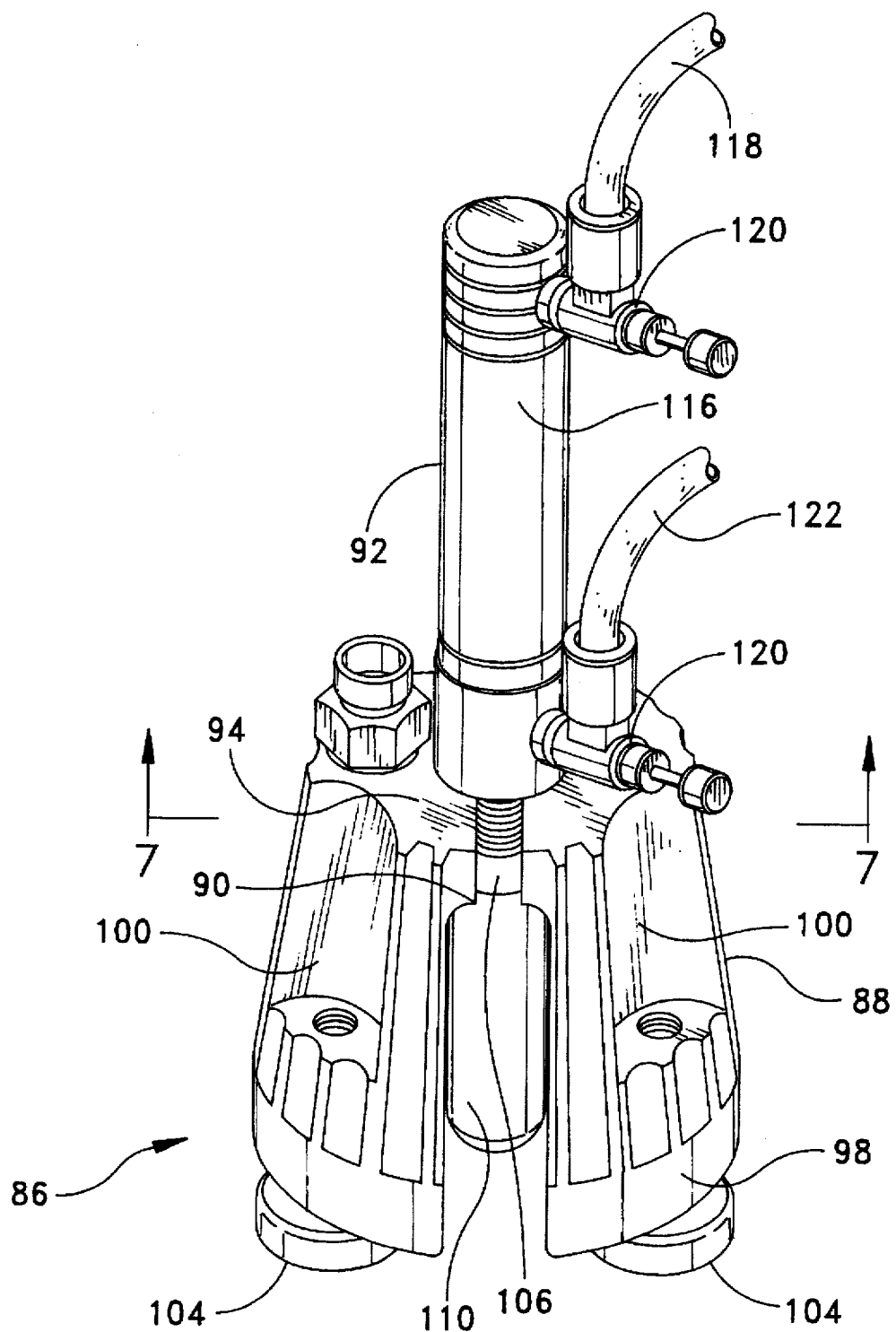
FIG. 6 is a perspective view of an impactor head device of another preferred embodiment.
Figure 7:
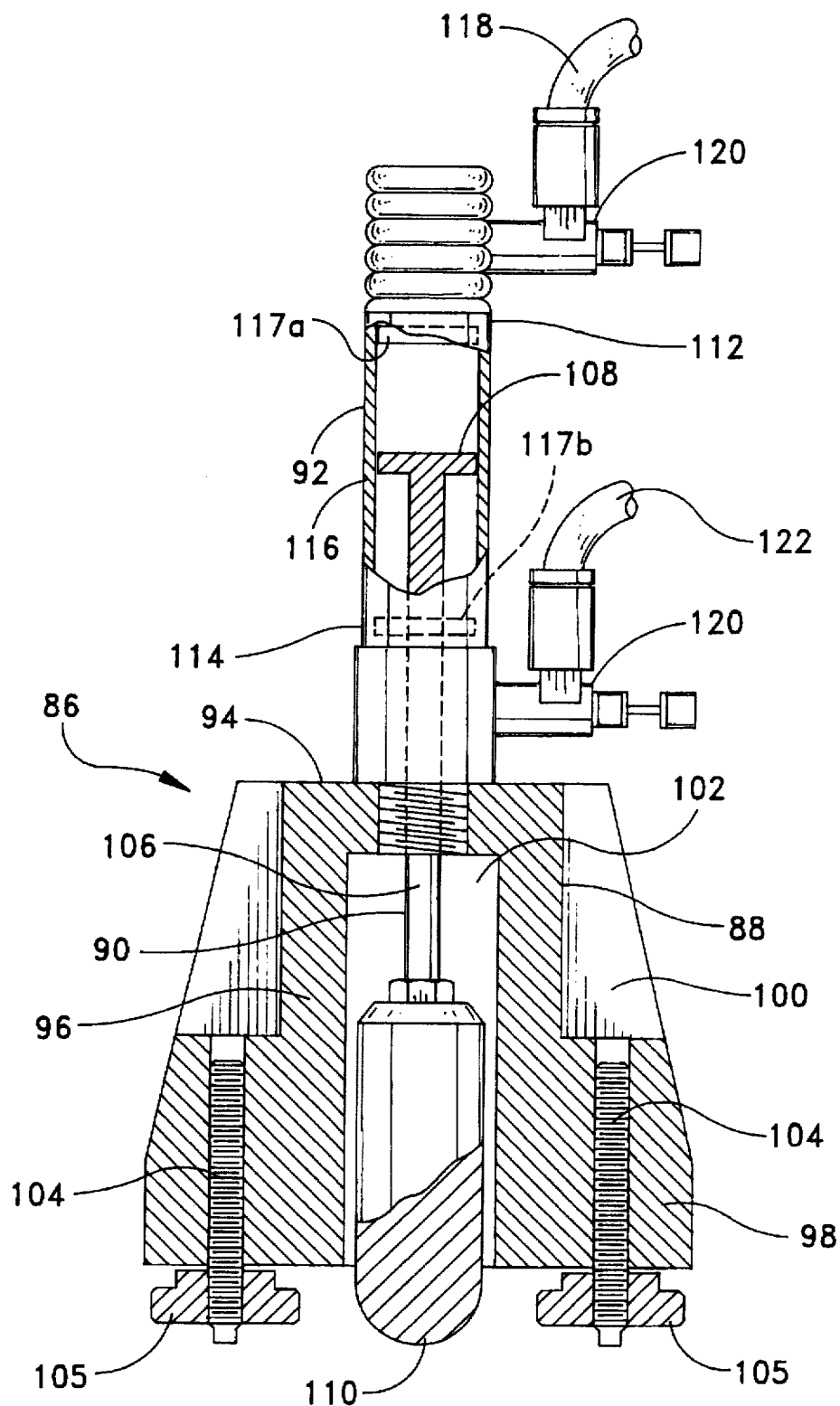
FIG. 7 is a cross-sectional view taken along line 7—7 of FIG. 6.

Referring to FIGS. 6 and 7, there is generally indicated at 86 an impactor head device of another preferred embodiment. More specifically, impactor head device 86 is a heavy-duty version of device 12, and is designed for testing relatively thick and heavy structures. As shown, the device 86 includes a housing 88, an impactor head 90 disposed within the housing 88, and a double acting cylinder 92 mounted on top of the housing 88. The housing 88 includes an inverse U-shaped body defined by a top wall 94, a cylindrically-shaped wall 96, and an outwardly projecting bottom wall 98. A plurality of gussets 100 project outwardly from the cylindrically-shaped 96 wall for structural and operator gripping purposes. The cylindrically-shaped wall 96 defines a cavity 102 that receives the impactor head 90 therein. The bottom wall 98 includes a plurality of non-marring positioning elements 104 which are threadably installed in the bottom of the housing 98, their extension is fixed after adjustment by the knurled locking collars 105. Each positioning element 104 has a non-marring end which is capable of sliding across the test surface.

Referring particularly to FIG. 7, the impactor head 90 includes an elongate shaft 106 having a piston 108 formed at its upper end. The lower end of the shaft 106 of the impactor head 90 is suitably releasably connected to a blunt impactor head member 110. The arrangement of the impactor head 90 is nearly identical as the impactor head 22 of device 12 with the exception that the impactor head member 110 of the device illustrated in FIG. 7 is larger and heavier than the impactor head member 38 of device 12.

The cylinder 92 is mounted coaxially on the top wall 94 of the housing 88 with respect to the cylindrically-shaped wall 96 of the housing 88. The cylinder 92 includes a top head wall 112, a bottom head wall 114 spaced from the top head wall 112 and suitably attached to the top wall 94 of the housing 88, and a cylindrical wall 116 integrally formed with the top and bottom head walls 112, 114. Bumpers 117a, 117b are also provided for cushioning the piston 108 during its upstroke and downstroke within the cylinder 92. These bumpers 117a, 117b operate in the same manner as bumpers 53a, 53b of device 12.

A first line 118 is in fluid communication with a port (not shown) formed in the top head wall 112 of the cylinder 92 via a valve 120. Similarly, a second line 122 is in fluid communication with a port (not shown) formed in the bottom head wall 114 via another valve also indicated at 120. The piston 108 of the impactor head 90 is disposed within the cylinder 92; and upon either the first control 14 or the second control 16 delivering fluid to the first line 118, fluid is delivered to the cylinder 92 above the piston 108 for moving the impactor head 90 downwardly. This motion of the piston 108 causes the impactor head member 110 to strike the structural member being tested. Control knobs (not designated) are provided on each valve 120 for controlling the rate at which the impactor head member 110 travels or reciprocates within the cylinder. After the impact, fluid is then delivered by the first or second control 14, 16 to the second line 122 thereby delivering fluid into the cylinder 92 below the piston 108 for moving the impactor head 90 upwardly to its retracted position. As described above, the impact absorbing bumpers 117a, 117b are placed at the extend and retract limits of the piston stroke to reduce spurious noise generated by cylinder cycling and metal to metal contact between the piston 108 and the upper and lower head walls 112, 114.

Figure 8:
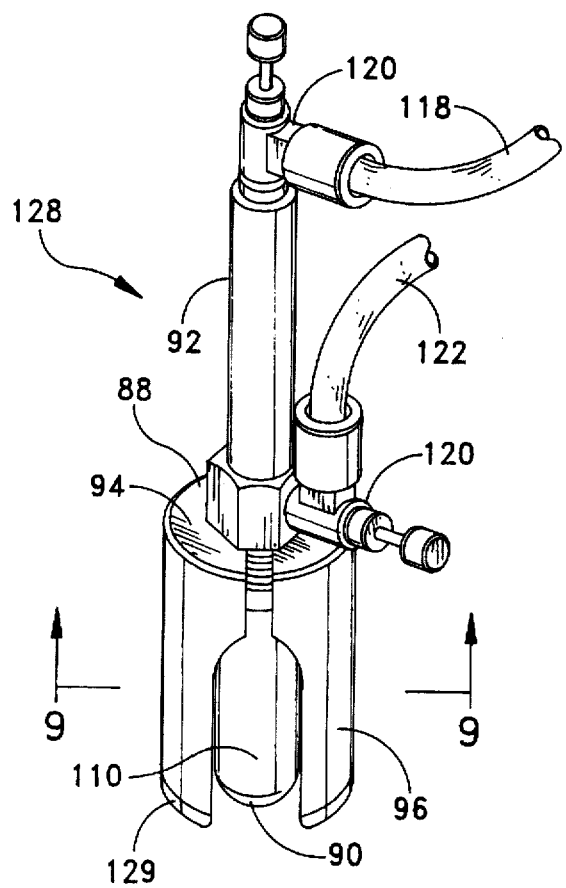
FIG. 8 is a perspective view of an impactor head device of yet another preferred embodiment.
Figure 9:
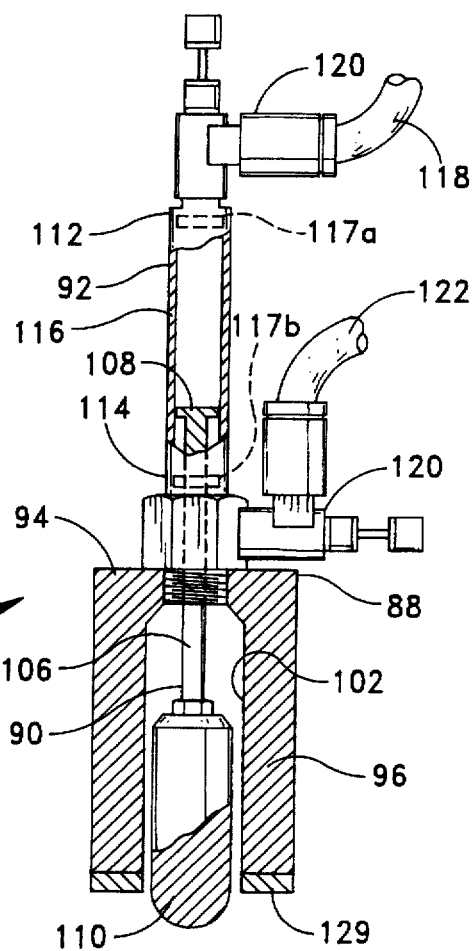
FIG. 9 is a cross-sectional view taken along line 9—9 of FIG. 8.

Turning now to FIGS. 8 and 9, there is generally indicated at 128 an impactor head device of yet another preferred embodiment. This device 128 is constructed nearly identically as device 86 wherein similar reference characters designate corresponding parts between device 86 and device 128. As shown, the main difference between device 128 and devices 12 and 86 is that device 128 is smaller in size for testing structures with lighter impacts than the devices 12, 86 and is suitable for thin walled structures, and lacks the vacuum drawing means of device 12. As shown, the device 128 includes a low friction polymeric facing 129 provided on the lower end of the cylindrically-shaped wall 96 so that the test device is easily slid over polished or painted surfaces for rapid assessment of the surface without inflicting cosmetic damage thereto. The impactor head device 128 of the embodiment illustrated in FIGS. 8 and 9 is especially suited for areas of light construction or areas having limited access and/or space constraints.

As mentioned briefly above, each device 12, 86, and 128, includes a means embodying an acoustic transducer 130 for generating and transmitting an electrical signal based on the acoustic signature of the impactor head strike (38 or 110) against the structural member being tested. Referring specifically to FIG. 1, and to FIG. 10, the acoustic transducer 130 is de-coupled from the impactor device 12, 86 or 128 and can be mounted on the operator, support hoses, control 18, etc. The acoustic transducer 130 generates an electrical signal when the impactor head 90 strikes the test item and transmits the signal via a cable 132 to a tape recording machine 134 (see FIG. 10). An amplifier or signal conditioner (not shown) can be provided for amplifying the acoustic signal generated by the acoustic transducer 130.

Figure 10:
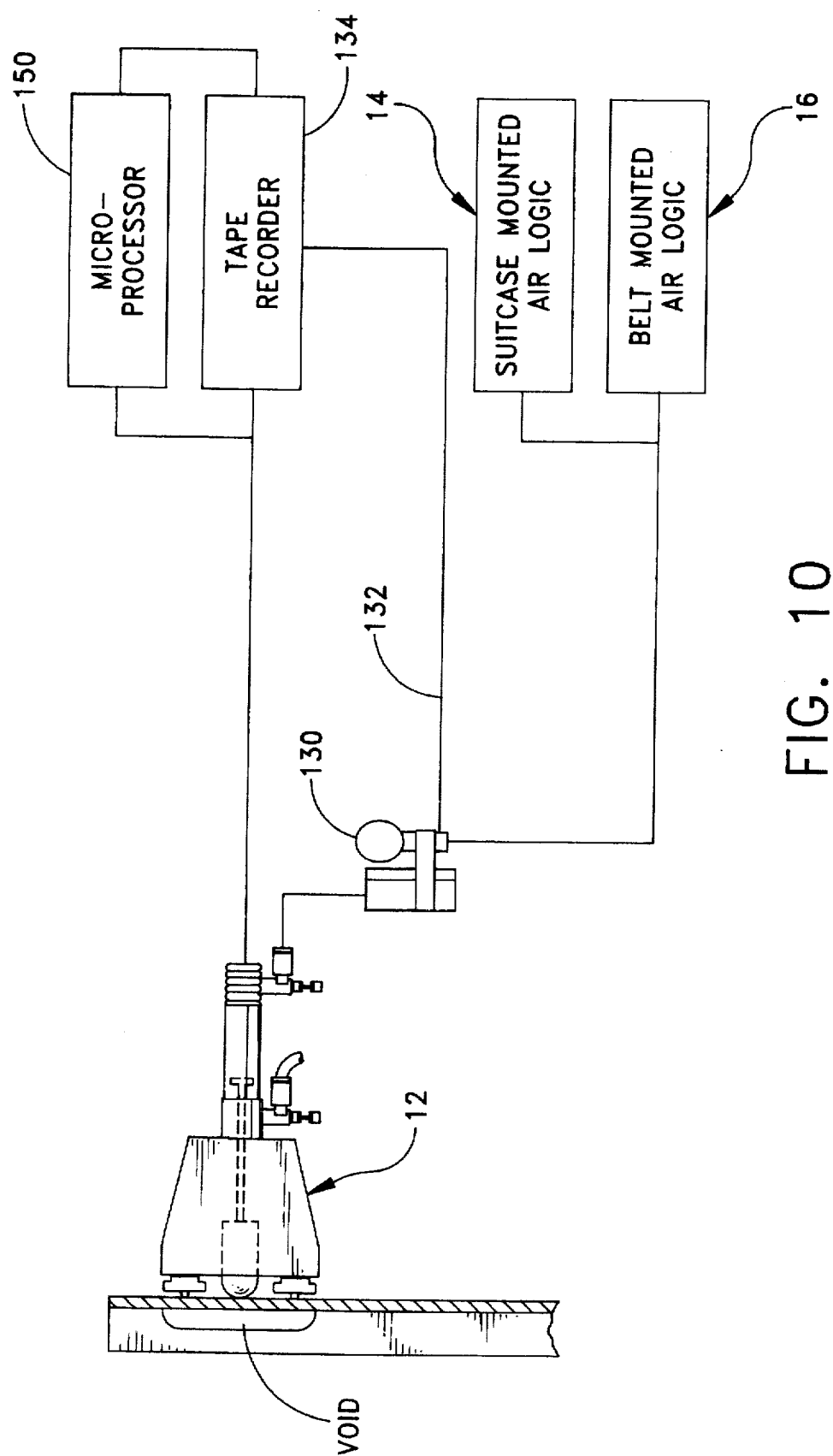
FIG. 10 is a view of the impactor head device in electrical communication with a tape recording machine or hard disk of the apparatus.

It should be understood that the acoustic transducer 130 can be located anywhere near the point of impact and still fall within the scope of the present invention. For example, the acoustic transducer 130 can be embodied in a unit which is hand-held by the operator, mounted on the operator's body, held by an accessory, fixture, etc., and positioned proximate the point of impact. Furthermore, it should be noted that the acoustic transducer 130 can be hard wired directly to an A/D card 136 (see FIG. 11) instead of the tape recording machine 134 and still fall within the scope of the present invention. As shown in FIG. 10, the device 12 is in communication with either the first or second controls 14, 16 for controlling movement of the impactor head 22.

Figure 11:
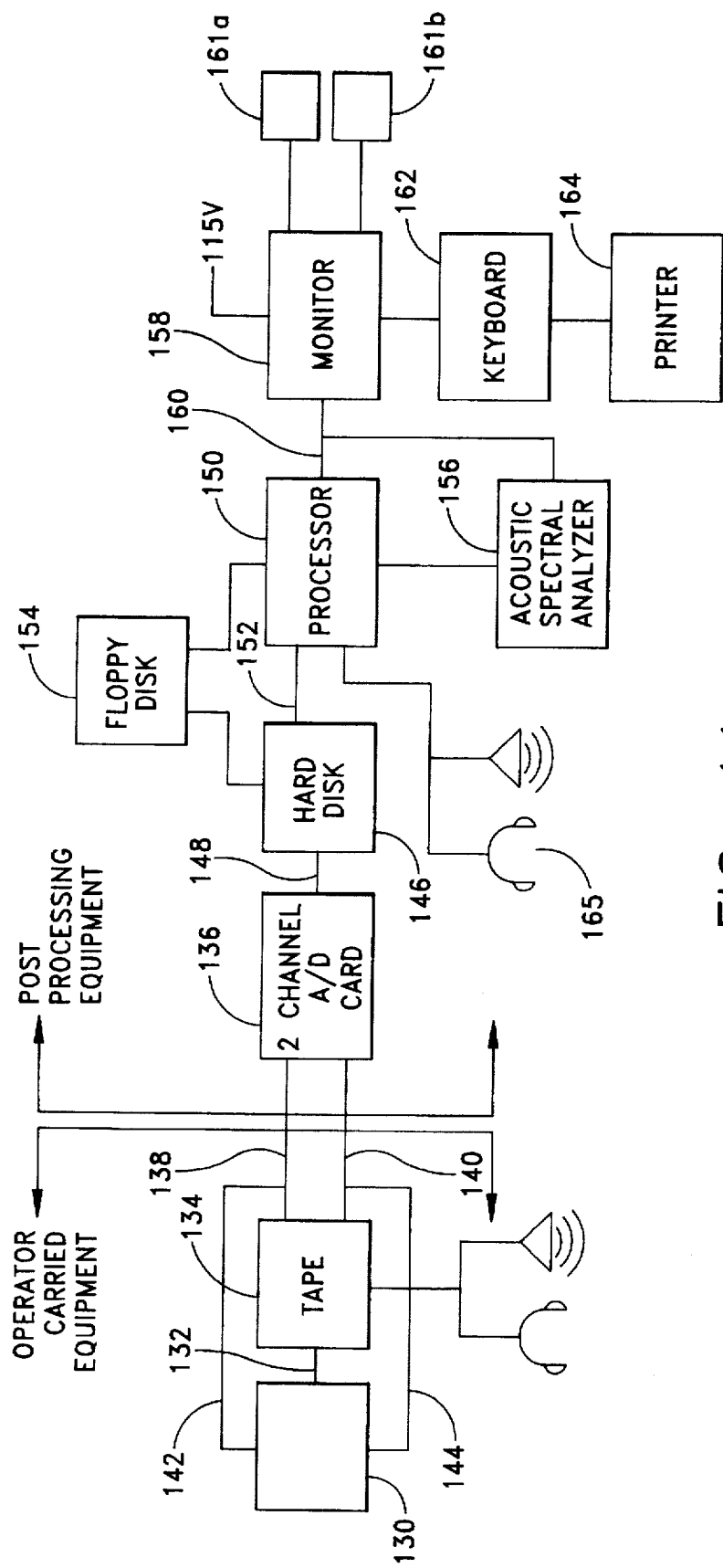
FIG. 11 is a schematic block diagram of the apparatus illustrated in FIG. 1.

Referring to FIG. 11, there is illustrated a schematic block diagram of the apparatus 10 after the acoustic signal is recorded by the tape recording machine 134. As shown, the tape recording machine 134 is in electrical communication with the A/D card 136 via lines 138, 140. Alternatively, the acoustic transducer 130, as mentioned above, can be hard wired to the A/D card 136 via lines 142, 144. In either event, the A/D card 136 converts the analog acoustic signal to a digital signal which is then preferably transmitted to a hard disk 146 via line 148.

The hard disc 146 is then placed within a microprocessor 150 which is represented by line 152. The digital signal is then read by the microprocessor 150, and can furthermore be saved on a high capacity storage media. The microprocessor 150 includes an acoustic spectral analyzer 156 for analyzing the digital signal. After analyzing the signal, the results are displayed on a monitor 158 in electrical communication with the microprocessor by line 160. It should be pointed out that the acoustic signals can be conditioned to highlight the differences between acceptable and damaged areas of the test surface. Various displays can also be utilized, such as a monocular/heads up display or a wrist mounted liquid crystal display illustrated by reference numerals 161a, 161b, respectively, in FIG. 11. A keyboard 162 and printer 164 can further be provided for manipulating the test results and printing a copy of the same. It should be noted that the schematic illustrated in FIG. 11 is but one way of converting the acoustic signal generated and transmitted by the acoustic transducer 130 and for displaying the signal in a presentable format and audible playback via headphones or speakers 165. Other methods are known in the art and are suitable for the purposes described herein.

Figure 12:
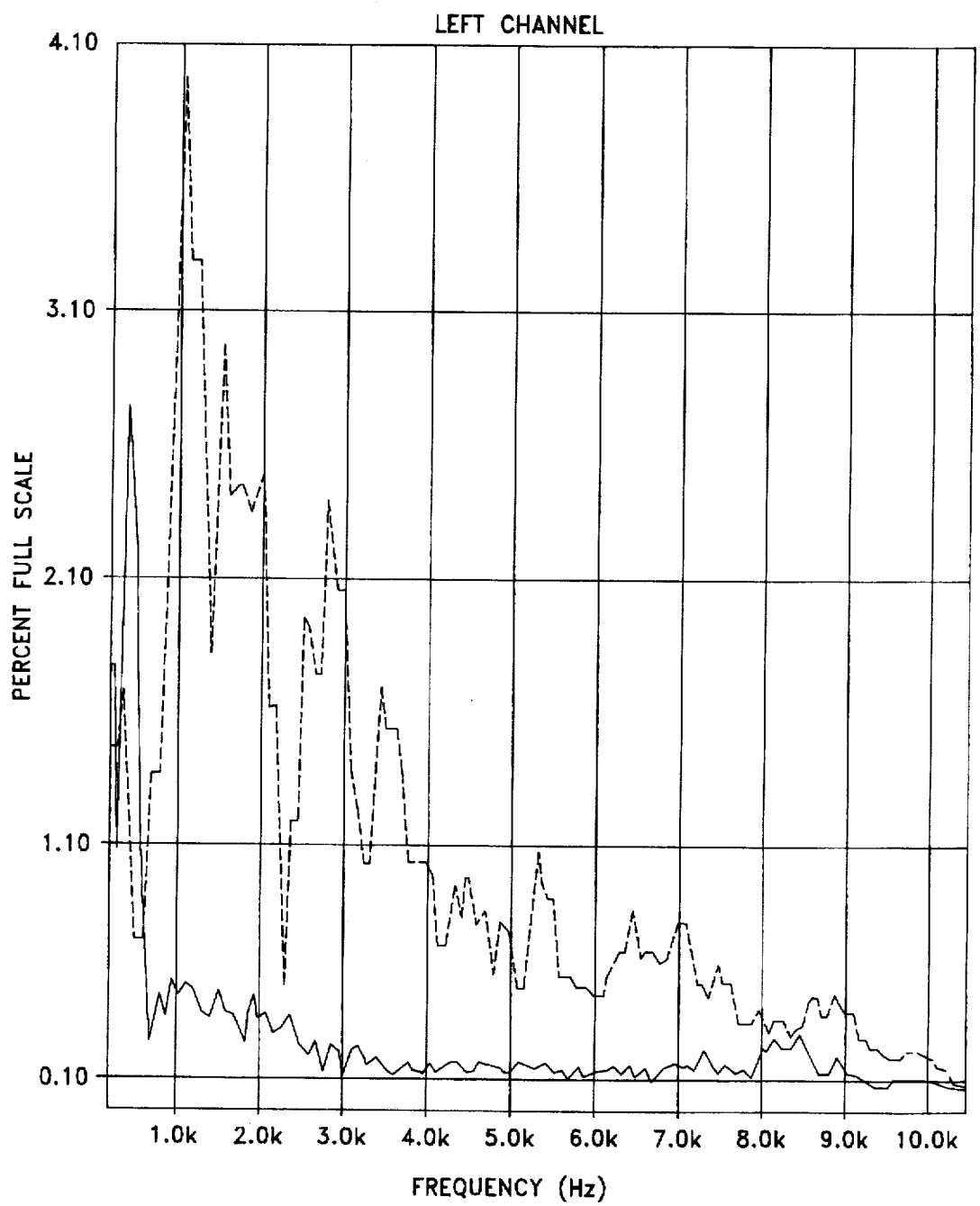
FIG. 12 is chart illustrating test results on a test surface.

FIG. 12 illustrates a representative test result. On the x-axis, the frequency of the impact is depicted. On the y-axis, the magnitude of the acoustic signal generated and transmitted by the acoustic transducer 130 is represented. As shown, the dotted line represents the acoustic signature of an impact on material which is structurally sound. The solid line depicts the acoustic signature of an impact at the same location after it was damaged. By comparing changes in the acoustic spectrum of the impacts between the good and damaged areas of the material being tested, damaged areas can be detected. Of course suitable training of the operators of the apparatus is required for ensuring that damaged areas are correctly noted and identified.

Referring back to FIG. 1, the components embodying the first and second controls 14, 16, and the microprocessor assembly 18 will be described in greater detail. As illustrated, the first control 16 includes a case 166 having a panel 168 and a pressure source (not shown) built therein or externally supplied. The case 166 can be fabricated from fiberglass reinforced plastic wherein o-rings are provided for sealing the case halves and fluid and electrical lines. Also, the case 166 is preferably leak tight when disposed under water, for example. The vacuum source described above can further be incorporated into the case 166. Provided on the panel 168 is a valve 170 for controlling the delivery of the fluid (e.g., air) from the pressure source to the first and second lines 48, 50 for the impactor head device 12. This valve 170 only controls the delivery of fluid into the lines 48, 50 and not the rate or speed of impacts of the impactor head 22. Gauge 172 is further provided for monitoring the pressure of the fluid contained in the pressure source. An adjustable, self-venting diaphragm-type regulator 173 is further provided for adjusting input pressure. The first control 14 also incorporates a filtering device (not shown). It should be observed that the pressure source can be embodied in an external unit separate from the case 166.

The second control 16 is especially suited for field use. More specifically, the second control 16 includes a padded, comfortable mount for logic controls 174 that is secured around the operator's waist by an adjustable belt or harness, for example. Secured to the sheet 174 are a canister 176 containing air logic and fluid under pressure, a gauge 178 for displaying the inlet pressure of the fluid to the canister 176 as controlled by a regulator 179, and a valve 180 for delivering pressurized fluid to the first and second lines 48, 50. As previously described, the rate at which the impact device 12 operates is adjusted by the knobs 181 provided on the controls 14, 16. The second control 16 is balanced and mounted on an anatomically contoured padded plate, secured around the operator's waist or chest areas in a position that does not inhibit the crawling, kneeling and other operator contortions common to field inspections of large military and commercial structures. Either the first control 14 or the second control 16 can be used effectively for producing adequate test results.

Still referring to FIGS. 1 and 11, the microprocessor assembly 18 includes the aforementioned microprocessor 150, acoustic analyzer 156, monitor 158, and keyboard 162. Further included in the assembly is a hard disk drive 182 for receiving the disk 146. As shown, the tape recording machine 134 is in electrical communication with the microprocessor 150 by cable 184.

In operation, any of the three impactor head devices 12, 86 or 128 described above can be used for hammer sounding a structural member requiring testing. Device 12 is especially suited for particular uses since the attachment fixtures 68 are releasably attached to the mounting plate 54 depending on the contour of the structural member being tested. For example, if an outside corner is to be tap tested, the attachment fixture 68c as illustrated in FIG. 5C can be utilized. If for example, a flat or gently curved surface of the structural member requires testing, and the surface is relatively rough, the device 86 depicted in FIGS. 6 and 7 can be used. Device 128 of FIGS. 8 and 9 is suitable for use where access is restricted, or for thin skinned or lightly constructed components or small components requiring low energy impacts. In any event, each device 12, 86, or 128 can be used interchangeably with the apparatus 10 and still fall within the scope of the present invention.

After a suitable impactor head is chosen, the operator can choose between the first and second controls 14, 16. The first control 14 housed by case 166 is suitable for use when space constraints are not present, or in rough service conditions, when a splash resistant or waterproof housing for the control logic and tape recorder is required. The second control 18 is ergonomically designed for ease of use outdoors, on staging, etc., by the operator over large areas requiring testing, thereby giving the operator the freedom required to move great distances without having to move the case 166 of the first control 14. With either the first control 14 or the second control 16, the operator first positions the impactor head device 12, 86, or 128 on the structural member requiring testing, and for the device 12 illustrated in FIGS. 2–5, chooses the appropriate fixture attachment 68. For the device 86 illustrated in FIGS. 1, 6 and 7, the operator adjusts the non-marring positioning elements 104 so as to normalize the unit relative to rough or contoured test surfaces. For the device illustrated in FIGS. 2 and 3, mounted on a flat plate, or mounted on adapted plates of FIGS. 5A–5E, the elastomeric gasket 72 on the fixture 68 is used to establish a vacuum seal. Also, as illustrated in FIG. 4, the non-marring positioning elements 78 can be used to permit a dual function head—sliding when extending shaft portions 80 are extended so that ends 82 engage the surface, or vacuum attached when portions 80 are retracted and the gasket 72 seals against the surface. It should be noted that the tapping force rate, impactor head materials and adaptor bases are all easily interchangeable with a minimum need for tools so as to tune the hammer mechanism to generate returns that maximize the acoustic disparities between intact and damaged areas.

Once the impactor head device 12, 86, Or 128 is correctly positioned, the operator can begin the operation of the apparatus 10. Referring to FIG. 10, the acoustic signature of the strikes of the impactor head 22 or 90 against the structural member is captured by the acoustic transducer 130 and recorded by the tape recorder machine 134. As mentioned above, it is also within the scope of the present invention to send the acoustic signals directly to the microprocessor 150 via lines 142 and 144 (FIG. 11). However, the arrangement illustrated in FIG. 10 allows the operator to tape record the acoustic signature with a relatively small, lightweight and inexpensive tape recording machine 134 at the test site, rather than subjecting the microprocessor assembly 18 to any adverse conditions present at the test site. Hardened microprocessing equipment suitable for field work and harsh environments is available.

After the testing is concluded, the operator converts the analog acoustic signature to digital signals by the A/D card 136 or process digitized sound files on the hard drive. The digital signals are then stored on a hard disk 146 and then can be read by the microprocessor 150 wherein an acoustic spectral analyzer 156 examines the data. The results can then be displayed on the monitor 158 and printed out on the printer 164. The results also can be played back via the headphones or speakers 165 before and after they are displayed on the monitor 158 for comparing the results and for interpreting them. In this regard, the test results can be compared with prior test results of good or undamaged areas, or with known test results, so as to enable the operator to determine whether the tested area is damaged.

Thus, it should be observed that the apparatus 10 of the present invention provides a practical and quantified means to tap test to emphasize the structural integrity of both large and small and complex-shaped structures under realistic service conditions. It can therefore be seen that for these reasons, the instant invention is believed to represent a significant advancement in the art which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A portable test hammer apparatus for damage assessment of a structure member, said apparatus comprising:
    an impactor head device having a housing sized to be held in a human hand and engageable with the structural member, an impactor head disposed within the housing for reciprocating movement therein, and low noise moving means for moving the impactor head in a reciprocating manner from a retracted position within the housing to a projected position in which the impactor head impacts the structural member; and
    an acoustic transducer de-coupled from the impactor head of the impactor head device for generating and transmitting an acoustic signal based on the sound of the impact of the impactor head against the structural member.

2. An apparatus as set forth in claim 1, said housing having an upper head wall, a lower head wall spaced from the upper head wall, and a cylindrical wall attached at its upper end to the upper head wall and attached at its lower end to the lower head wall.

3. An apparatus as set forth in claim 2, said cylindrical wall defining a chamber therein, said moving means comprising a piston attached to said impactor head, said piston being disposed within said chamber for reciprocating movement therein.

4. An apparatus as set forth in claim 3, said impactor head being attached to said piston by a shaft integrally formed with the piston.

5. An apparatus as set forth in claim 3, said moving means further comprising fluid delivery means in fluid communication with said chamber.

6. An apparatus as set forth in claim 5, said fluid delivery means comprising a first line connected to a first port formed in the cylindrical wall so as to deliver fluid into the chamber above the piston and a second line connected to a second port formed in the cylindrical wall so as to deliver fluid into the chamber below the piston.

7. An apparatus as set forth in claim 6 further comprising control means for controlling the fluid delivering means.

8. An apparatus as set forth in claim 7, said control means comprising a control case having a valve for controlling the delivery of fluid into the first and second ports.

9. A portable test hammer apparatus for damage assessment of a structural member, said apparatus comprising:
    an impactor head device having a housing sized to be held in a human hand and engageable with the structural member, an impactor head disposed within the housing for reciprocating movement therein, and moving means for moving the impactor head from a retracted position within the housing to a projected position in which the impactor head impacts the structural member, said housing having an upper head wall, a lower head wall spaced from the upper head wall, and a cylindrical wall attached at its upper end to the upper head wall and attached at its lower end to the lower head wall; and
    signal means for generating and transmitting an acoustic signal based on the sound of the impact of the impactor head against the structural member,
    said housing further comprising a mounting plate attached to the lower head wall, said mounting plate having means for releasably securing thereto an attachment fixture for engaging the structural member.

10. An apparatus as set forth in claim 9, said attachment fixture having a body with a surface which corresponds with the surface of the structural member.

11. An apparatus as set forth in claim 10, said attachment fixture further having a plurality of positioning elements secured to body for registering on the surface of the structural member thereby adjusting the height of the body relative to structural member.

12. A portable test hammer apparatus for damage assessment of a structural member, said apparatus comprising:
    an impactor head device having a housing sized to be held in a human hand and engageable with the structural member, an impactor head disposed within the housing for reciprocating movement therein, and moving means for moving the impactor head from a retracted position within the housing to a projected position in which the impactor head impacts the structural member, said housing further having means for drawing the housing of the impactor head device against the surface of the structural member; and signal means for generating and transmitting an acoustic signal based on the sound of the impact of the impactor head against the structural member.

13. An apparatus as set forth in claim 12, said drawing means comprising an elastomeric seal secured to the lower head wall of the housing, and a vacuum source in fluid communication with the housing.

14. An apparatus as set forth in claim 1 further comprising displaying means, in electrical communication with the signal means, for visually displaying the acoustic signal.

15. An apparatus as set forth in claim 14, said displaying means comprising a microprocessor and a screen monitor in electrical communication with the screen monitor.

16. Art apparatus as set forth in claim 1 further comprising means, in electrical communication with the generating and transmitting means, for storing the acoustic signal.

17. Art apparatus as set forth in claim 16, said storing means comprising an analog or digital tape recorder.

18. An apparatus as set forth in claim 1, said acoustic transducer being located proximate to the impactor head.

19. A portable test hammer apparatus for damage assessment the structural integrity of a structural member, said apparatus comprising:

a housing sized for being received within a human hand, the housing having a surface for mating with the structural member being tested;

an impactor head disposed within the housing for reciprocating movement with respect to the housing, the impactor head being adapted to impact the structural member being tested upon achieving a downward movement;

means for controlling the movement of the impactor head against the structural member; and an acoustic transducer positioned proximate to the point of impact of the impactor head against the structural member.

20. An apparatus as set forth in claim 19 further comprising a monitor for observing the acoustic signature of the impact of the impactor head against the structural member, the monitor being in electrical communication with the acoustic transducer.

* * * * *